United States Patent
Choi et al.

(10) Patent No.: US 10,059,985 B2
(45) Date of Patent: Aug. 28, 2018

(54) METHOD OF AMPLIFYING TELOMERE

(71) Applicant: Samsung Electronics Co., Ltd., Suwon-si, Gyeonggi-do (KR)

(72) Inventors: Kobong Choi, Osan-si (KR); Hyuntae Kang, Seoul (KR); Jungwon Keum, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 223 days.

(21) Appl. No.: 14/866,386

(22) Filed: Sep. 25, 2015

(65) Prior Publication Data

US 2016/0090620 A1    Mar. 31, 2016

(30) Foreign Application Priority Data

Sep. 26, 2014 (KR) .................. 10-2014-0129519

(51) Int. Cl.
*C12Q 1/68* (2018.01)
*C12P 19/34* (2006.01)
*C12Q 1/6862* (2018.01)
*C12Q 1/6855* (2018.01)

(52) U.S. Cl.
CPC ......... *C12Q 1/6862* (2013.01); *C12Q 1/6855* (2013.01)

(58) Field of Classification Search
None
See application file for complete search history.

(56) References Cited

U.S. PATENT DOCUMENTS

| | | | |
|---|---|---|---|
| 5,741,677 A | 4/1998 | Kozlowski et al. | |
| 9,546,938 B2 | 1/2017 | Kim et al. | |
| 9,745,614 B2 * | 8/2017 | Schroeder | C12Q 1/6806 |
| 2004/0265815 A1 | 12/2004 | Baird | |
| 2011/0244462 A1 | 10/2011 | Bendix et al. | |
| 2012/0196284 A1 | 8/2012 | Aviv et al. | |
| 2014/0057322 A1 | 2/2014 | Choi et al. | |
| 2014/0093880 A1 | 4/2014 | Kim et al. | |

FOREIGN PATENT DOCUMENTS

WO    2012/135125 A1    10/2012

OTHER PUBLICATIONS

Bendix et al., "The load of short telomeres, estimated by a new method, Universal STELA, correlates with number of senescent cells", *Aging Cell*, 9: 383-397 (2010).

* cited by examiner

*Primary Examiner* — Young J Kim
(74) *Attorney, Agent, or Firm* — Leydig, Voit & Mayer, Ltd.

(57) ABSTRACT

A method of amplifying a telomere of genomic DNA using an adaptor sequence, and a composition and a kit for amplifying the telomere of genomic DNA.

9 Claims, 5 Drawing Sheets

Specification includes a Sequence Listing.

SEQUENCE LISTING

```
<160> NUMBER OF SEQ ID NOS: 21

<210> SEQ ID NO 1
<211> LENGTH: 6
<212> TYPE: DNA
<213> ORGANISM: Artificial Sequence
<220> FEATURE:
<223> OTHER INFORMATION: Synthetic telomere nucleic acid sequence

<400> SEQUENCE: 1 ttaggg                                                          6

<210> SEQ ID NO 2
<211> LENGTH: 6
<212> TYPE: DNA
<213> ORGANISM: Artificial Sequence
```

```
<220> FEATURE:
<223> OTHER INFORMATION: Synthetic telomere fragment sequence

<400> SEQUENCE: 2 cctaac                                                                    6

<210> SEQ ID NO 3
<211> LENGTH: 6
<212> TYPE: DNA
<213> ORGANISM: Artificial Sequence
<220> FEATURE:
<223> OTHER INFORMATION: Synthetic First region of single strand adaptor
      nucleic acid

<400> SEQUENCE: 3 aaccct                                                                    6

<210> SEQ ID NO 4
<211> LENGTH: 6
<212> TYPE: DNA
<213> ORGANISM: Artificial Sequence
<220> FEATURE:
<223> OTHER INFORMATION: Synthetic First region of single strand adaptor
      nucleic acid

<400> SEQUENCE: 4 ctaacc                                                                    6

<210> SEQ ID NO 5
<211> LENGTH: 6
<212> TYPE: DNA
<213> ORGANISM: Artificial Sequence
<220> FEATURE:
<223> OTHER INFORMATION: Synthetic First region of single strand adaptor
      nucleic acid

<400> SEQUENCE: 5 taaccc                                                                    6

<210> SEQ ID NO 6
<211> LENGTH: 6
<212> TYPE: DNA
<213> ORGANISM: Artificial Sequence
<220> FEATURE:
<223> OTHER INFORMATION: Synthetic First region of single strand adaptor
      nucleic acid

<400> SEQUENCE: 6 acccta                                                                    6

<210> SEQ ID NO 7
<211> LENGTH: 6
<212> TYPE: DNA
<213> ORGANISM: Artificial Sequence
<220> FEATURE:
<223> OTHER INFORMATION: Synthetic First region of single strand adaptor
      nucleic acid

<400> SEQUENCE: 7 ccctaa                                                                    6

<210> SEQ ID NO 8
<211> LENGTH: 48
<212> TYPE: DNA
<213> ORGANISM: Artificial Sequence
<220> FEATURE:
<223> OTHER INFORMATION: Synthetic single strand adaptor nucleic acid
```

-continued

<400> SEQUENCE: 8
agatcggaag agctcgtatg ctgctccgtg catctggcat cccctaac        48

<210> SEQ ID NO 9
<211> LENGTH: 48
<212> TYPE: DNA
<213> ORGANISM: Artificial Sequence
<220> FEATURE:
<223> OTHER INFORMATION: Synthetic single strand adaptor nucleic acid

<400> SEQUENCE: 9
agatcggaag agctcgtatg ctgctccgtg catctggcat ctaaccct        48

<210> SEQ ID NO 10
<211> LENGTH: 48
<212> TYPE: DNA
<213> ORGANISM: Artificial Sequence
<220> FEATURE:
<223> OTHER INFORMATION: Synthetic single strand adaptor nucleic acid

<400> SEQUENCE: 10
agatcggaag agctcgtatg ctgctccgtg catctggcat ctctaacc        48

<210> SEQ ID NO 11
<211> LENGTH: 48
<212> TYPE: DNA
<213> ORGANISM: Artificial Sequence
<220> FEATURE:
<223> OTHER INFORMATION: Synthetic single strand adaptor nucleic acid

<400> SEQUENCE: 11
agatcggaag agctcgtatg ctgctccgtg catctggcat cttaaccc        48

<210> SEQ ID NO 12
<211> LENGTH: 48
<212> TYPE: DNA
<213> ORGANISM: Artificial Sequence
<220> FEATURE:
<223> OTHER INFORMATION: Synthetic single strand adaptor nucleic acid

<400> SEQUENCE: 12
agatcggaag agctcgtatg ctgctccgtg catctggcat ctacccta        48

<210> SEQ ID NO 13
<211> LENGTH: 48
<212> TYPE: DNA
<213> ORGANISM: Artificial Sequence
<220> FEATURE:
<223> OTHER INFORMATION: Synthetic single strand adaptor nucleic acid

<400> SEQUENCE: 13
agatcggaag agctcgtatg ctgctccgtg catctggcat ctccctaa        48

<210> SEQ ID NO 14
<211> LENGTH: 21
<212> TYPE: DNA
<213> ORGANISM: Artificial Sequence
<220> FEATURE:
<223> OTHER INFORMATION: Synthetic Forward primer

<400> SEQUENCE: 14
tgctccgtgc atctggcatc t                                     21

<210> SEQ ID NO 15

```
<211> LENGTH: 21
<212> TYPE: DNA
<213> ORGANISM: Artificial Sequence
<220> FEATURE:
<223> OTHER INFORMATION: Synthetic Backward primer

<400> SEQUENCE: 15
gcatacgagc tcttccgatc t                                              21

<210> SEQ ID NO 16
<211> LENGTH: 23
<212> TYPE: DNA
<213> ORGANISM: Artificial Sequence
<220> FEATURE:
<223> OTHER INFORMATION: Synthetic Forward primer for control gene

<400> SEQUENCE: 16
cagcaagtgg gaaggtgtaa tcc                                            23

<210> SEQ ID NO 17
<211> LENGTH: 25
<212> TYPE: DNA
<213> ORGANISM: Artificial Sequence
<220> FEATURE:
<223> OTHER INFORMATION: Synthetic Backward primer for control gene

<400> SEQUENCE: 17
cccattctat catcaacggg tacaa                                          25

<210> SEQ ID NO 18
<211> LENGTH: 7
<212> TYPE: DNA
<213> ORGANISM: Artificial Sequence
<220> FEATURE:
<223> OTHER INFORMATION: Synthetic telomere nucleic acid sequence

<400> SEQUENCE: 18 tttaggg                                                               7

<210> SEQ ID NO 19
<211> LENGTH: 10
<212> TYPE: DNA
<213> ORGANISM: Artificial Sequence
<220> FEATURE:
<223> OTHER INFORMATION: Synthetic telomere nucleic acid sequence

<400> SEQUENCE: 19 tttttttaggg                                                          10

<210> SEQ ID NO 20
<211> LENGTH: 5
<212> TYPE: DNA
<213> ORGANISM: Artificial Sequence
<220> FEATURE:
<223> OTHER INFORMATION: Synthetic telomere nucleic acid sequence

<400> SEQUENCE: 20 ttagg                                                                 5

<210> SEQ ID NO 21
<211> LENGTH: 6
<212> TYPE: DNA
<213> ORGANISM: Artificial Sequence
```

```
<220> FEATURE:
<223> OTHER INFORMATION: Synthetic telomere nucleic acid sequence

<400> SEQUENCE: 21 ttaggc                                                                    6
```

METHOD OF AMPLIFYING TELOMERE

RELATED APPLICATION

This application claims the benefit of Korean Patent Application No. 10-2014-0129519, filed on Sep. 26, 2014, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,022 Byte ASCII (Text) file named "721435_ST25.TXT," created on Sep. 25, 2015.

BACKGROUND

1. Field

The present disclosure relates to methods of amplifying telomeres of genomic DNA and compositions and kits for amplifying telomeres of genomic DNA used therefor.

2. Description of the Related Art

In eukaryotic cells, lagging strands of DNA get shorter by DNA amplification due to an end replication problem related to the DNA amplification. This is caused as a result of a DNA replication mechanism. During replication of a lagging strand, a short RNA sequence acting as a primer binds ahead on the lagging strand. DNA polymerases initiate replication from several origins of replication forming Okazaki fragments. Several RNA primers bind to one lagging strand of DNA, and DNA polymerases and DNA ligases come along to convert the RNA primers to DNA, and to seal the gaps between the Okazaki fragments. In order to replace the RNA with DNA, a DNA fragment should be located at a region directly upstream from the RNA primer. This occurs at every locations of the lagging strand except for an end of chromosome to which a last RNA primer binds. As a result, the RNAs are degraded by RNases which degrade RNA on DNA, and the telomere that is an end portion of chromosomal DNA is partially lost during each cycle of replication. When telomeres in a cell get too short, the cell can no longer replicate and apoptosis occurs. Thus, the length of the telomere is estimated as a factor determining aging and life span and estimated to be related to prevention of cancers.

Due to roles of telomeres in cancers and aging-related diseases, information about lengths of telomeres is required. The lengths of the telomeres may be determined by telomere restriction fragment length assay (TRF), primer extension assay, quantitative polymerase chain reaction (q-PCR), single telomere elongation length analysis (STELA), universal STELA, and the like. However, there remains a need to develop improved methods of determining the length of a telomere of genomic DNA with high efficiency and high sensitivity.

SUMMARY

Provided are methods of amplifying telomeres of genomic DNA, as well as compositions and kits useful for such a method.

In one aspect, the method of amplifying a telomere of genomic DNA includes: preparing a telomere fragment by incubating a sample including genomic DNA including a telomere with at least one nuclease; preparing a telomere fragment-adaptor n ligated product by incubating the telomere fragment with a single stranded adaptor nucleic acid and a ligase, wherein the single stranded adaptor nucleic acid includes a first region complimentary to a nucleic acid sequence of the telomere or a fragment thereof; preparing a blunt-end telomere fragment-adaptor ligated product by incubating the telomere fragment-adaptor ligated product with an exonuclease, a first nucleic acid polymerase, or a combination thereof; preparing a circular telomere fragment-adaptor ligated product by incubating the blunt-end telomere fragment-adaptor ligated product in the presence of a ligase; and amplifying the telomere fragment by incubating the circular telomere fragment-adaptor ligated product in the presence of a primer and a second nucleic acid polymerase, wherein the primer is a forward primer including a nucleic acid sequence identical to at least two contiguous nucleotides located 5' of the first region of the single stranded adaptor nucleic acid, a reverse primer including a nucleic acid sequence complementary to the at least two contiguous nucleotides located 5' of the first region of the single stranded adaptor nucleic acid, or a combination thereof.

According to an aspect of another exemplary embodiment, a method of amplifying a telomere of genomic DNA includes: preparing a genomic DNA-adaptor ligated product by incubating a sample including genomic DNA including a telomere with a single stranded adaptor nucleic acid and a ligase, wherein the single stranded adaptor nucleic acid includes a first region complimentary to a nucleic acid sequence of the telomere or a fragment thereof; preparing a telomere fragment-adaptor ligated product by incubating the genomic DNA-adaptor nucleic acid ligated product with at least one nuclease; preparing a blunt end telomere fragment-adaptor ligated product by incubating the telomere fragment-adaptor ligated product with an exonuclease, a first nucleic acid polymerase, or a combination thereof; preparing a circular telomere fragment-adaptor ligated product by incubating the blunt end telomere fragment-adaptor ligated product with a ligase; and amplifying the telomere fragment by incubating the circular telomere fragment-adaptor ligated product with a primer and a second nucleic acid polymerase, wherein the primer is a forward primer including a nucleic acid sequence identical to at least two contiguous nucleotides located 5' of the first region of the single stranded adaptor nucleic acid, a reverse primer including a nucleic acid sequence complementary to the at least two contiguous nucleotides located 5' of the first region of the single stranded adaptor nucleic acid, or a combination thereof.

According to an aspect of another exemplary embodiment, a composition for amplifying a telomere of genomic DNA includes a single stranded adaptor nucleic acid including a first region complementary to a nucleic acid sequence of the telomere or a fragment thereof.

According to an aspect of another exemplary embodiment, a kit for amplifying a telomere of genomic DNA includes a single stranded adaptor nucleic acid including a first region complementary to a nucleic acid sequence of the telomere or a fragment thereof, and a primer.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list.

A method of amplifying a telomere of genomic DNA according to an exemplary embodiment includes:

preparing a telomere fragment by incubating a sample including genomic DNA including a telomere in the presence of at least one nuclease;

preparing a telomere fragment-adaptor nucleic acid ligated product by incubating the telomere fragment in the presence of a single stranded adaptor nucleic acid and a ligase, wherein the single stranded adaptor nucleic acid includes a first region complimentary to a nucleic acid sequence of the telomere or a fragment thereof;

preparing a telomere fragment-adaptor nucleic acid ligated product with a blunt end by incubating the telomere fragment-adaptor nucleic acid ligated product in the presence of an exonuclease, a first nucleic acid polymerase, or a combination thereof;

preparing a circular telomere fragment-adaptor nucleic acid ligated product by incubating the telomere fragment-adaptor nucleic acid ligated product with the blunt end in the presence of a ligase; and amplifying the telomere fragment by incubating the circular telomere fragment-adaptor nucleic acid ligated product in the presence of a primer and a second nucleic acid polymerase.

The primer can be a forward primer including a nucleic acid sequence identical to at least two contiguous nucleotides located 5' of the first region of the single stranded adaptor, a reverse primer including a nucleic acid sequence complementary to at least two contiguous nucleotides located 5' of the first region of the single stranded adaptor, or a combination thereof.

The method includes preparing a telomere fragment by incubating a sample containing genomic DNA including a telomere in the presence of at least one nuclease.

The genomic DNA includes a telomere. The term "genome" or "genomic DNA" refers to the genetic information carried by an organism in the nucleus. The genome may be a genome of a eukaryote. For example, eukaryotes may be vertebrates including mammals, fungi, slime mould, protozoa, higher plants, algae, insects, or yeast. For example, mammals may be humans, dogs, cows, horses, goats, mice, or rats. DNA is a deoxyribonucleic acid.

The term "telomere" refers to an end region of a chromosome including a nucleic acid with simple repetitive sequences and a protein. Since a linear DNA of a eukaryotic cell decreases in length with each replication, the telomere serves to protect the end of the chromosome. The repetitive sequence is referred to as a telomere nucleic acid sequence. The number of repeating sequences of the telomere nucleic acid sequence may vary in individual cells, and the number of repeating sequences of the telomere nucleic acid sequence is closely related to aging or cancer. Telomere nucleic acid sequences are well known in the art. For example, a vertebrate may have a telomere nucleic acid sequence in which any one of 5'-TTAGGG-3' (SEQ ID NO: 1), 5'-TTTAGGG-3' (SEQ ID NO: 18), 5'-TTTTTTAGGG-3' (SEQ ID NO: 19), 5'-TTAGG-3' (SEQ ID NO: 20), and 5'-TTAGGC-3' (SEQ ID NO: 21) is repeated.

The sample may be a biological sample. For example, the biological sample may be at least one selected from the group consisting of blood, saliva, urine, feces, tissues, cells, and biopsy materials. The sample may be a biological sample stored using a method well known in the art or nucleic acids isolated therefrom. The stored biological sample may be those stored for more than 1 year, e.g., from 1 to 10 years, and a frozen tissue sample or a formaline-fixed paraffin-embedded tissue sample stored at room temperature may be used as the biological sample. A method of isolating genomic DNA from the biological sample may be any method well known in the art.

The nuclease is an enzyme capable of cleaving a phosphodiester linkage within a nucleic acid. The nuclease may be a sequence-specific nuclease. The nuclease may be an endonuclease which cleaves an internal 3',5'-phosphodiester linkage of a polynucleotide chain or an exonuclease which cleaves nucleotides one at a time from a 5'-end or 3'-end of a polynucleotide chain. The nuclease may be a restriction enzyme. The restriction enzyme refers to an endonuclease that recognizes a specific nucleic acid sequence of DNA and cleaves a double strand thereof. The restriction enzyme recognizes a short nucleic acid sequence within a nucleic acid called a restriction enzyme recognition site. The restriction enzyme recognition site may be a polynucleotide including 4 nucleotides (hereinafter, called "nt"), 6 nt, or 8 nt. For example, the restriction enzyme may be Nde I, EcoRI, EcoRII, BamHI, HindIII, NotI, PvuII, SmaI, EcoRV, EcoP15I, KpnI, PstI, SacI, ScaI, SpeI, SphI, StuI, XbaI, or any combination thereof. The adaptor polynucleotide may not include the restriction enzyme recognition site. The restriction enzyme recognition site may be present in a site of the genome adjacent to the telomere. When the genomic DNA is cut using at least one restriction enzyme, the site of the genome adjacent to the telomere may be cut.

Incubation may be performed in vitro in the presence of the nuclease. Incubation may be performed at a temperature suitable for the restriction enzyme activity for a time period suitable for cleavage, e.g., for 10 minutes to 12 hours (overnight), for 1 hour to 12 hours (overnight), or for 3 hours to 12 hours (overnight). A composition of reactants may be determined in accordance with the nuclease or well known in the art.

The method includes preparing a telomere fragment-adaptor nucleic acid ligated product by incubating the telomere fragment in the presence of a single stranded adaptor nucleic acid and a ligase. In some aspects, only one adaptor is ligated to one end of the telomere fragment, such that the telomere fragment-adaptor nucleic acid ligated product comprises only one adaptor sequence ligated to one end of the telomere fragment.

The telomere fragment is a portion of a chromosome including a telomere.

The single stranded adaptor nucleic acid includes a first region complementary to a nucleic acid sequence of the telomere or a fragment thereof. The first region may be a region including a 3'-end of the single stranded adaptor nucleic acid. The single stranded adaptor nucleic acid may be DNA or RNA. The single stranded adaptor nucleic acid may also include a second region with a nucleic acid sequence as a forward primer, and a third region with a nucleic acid sequence complementary to a reverse primer, in order from the 3'-end of the adaptor nucleic acid. Thus, the second region is located 5' of the first region, and the third region is located 5' of the second region. The nucleic acid sequence of the adaptor nucleic acid is not complementary to the telomere, except for the first region of the adaptor nucleic acid. The first region may include at least one nucleic acid sequence selected from the group consisting of SEQ ID NOS: 2 to 7. The single stranded adaptor nucleic acid may be an adaptor nucleic acid including a first region with a nucleic acid sequence of SEQ ID NO: 2, an adaptor nucleic acid including a first region with a nucleic acid sequence of SEQ ID NO: 3, an adaptor nucleic acid including a first region with a nucleic acid sequence of SEQ ID NO: 4, an adaptor nucleic acid including a first region with a nucleic acid sequence of SEQ ID NO: 5, an adaptor nucleic acid including a first region with a nucleic acid sequence of SEQ ID NO: 6, an adaptor nucleic acid including a first region with a nucleic acid sequence of SEQ ID NO: 7, or any combination thereof. The single stranded adaptor nucleic acid may have a length, for example, of about 6 nt to about 60 nt, about 10 nt to about 55 nt, about 20 nt to about 50 nt, about 30 nt to about 50 nt, or about 40 nt to about 50 nt. The first region may have a length of, for example, about 2 nt to about 20 nt, about 4 nt to about 10 nt, or about 6 nt to about 8 nt.

The ligase is an enzyme that catalyzes the joining of nucleotides by forming a phosphodiester linkage by decomposing nucleoside triphosphate such as ATP. The ligase may be a DNA ligase. The DNA ligase may be T4 DNA ligase, T3 DNA ligase, T7 DNA ligase, E. coli DNA ligase, Ampligase DNA ligase, CIRCLIGASE™ ssDNA ligase, or any combination thereof. Incubation may be performed at a temperature suitable for the ligase activity for a time period suitable for ligation, e.g., for 10 minutes to 12 hours (overnight) or for 30 minutes to 12 hours (overnight).

The telomere fragment-adaptor nucleic acid ligated product may be a linear ligated product in which the telomere fragment and the first region of the adaptor nucleic acid complementarily bind to each other. When the nucleic acid sequence of the region of the adaptor nucleic acid other than the first region is not complementary to the telomere, the telomere fragment-adaptor nucleic acid ligated product may include a single stranded nucleic acid extending from the 3'-end of the telomere fragment that does not hybridize to the single stranded adaptor sequence 5' of the first region (see FIG. 1B).

The method includes preparing a telomere fragment-adaptor nucleic acid ligated product with a blunt end by incubating the telomere fragment-adaptor nucleic acid ligated product in the presence of an exonuclease, a first nucleic acid polymerase, or a combination thereof.

The term "exonuclease" refers to one of the nucleic acid cleaving enzymes capable of cleaving nucleotides one at a time from a 5'-end or 3'-end of a polynucleotide chain. For example, the exonuclease may be a single strand-specific exonuclease that specifically cleaves single stranded nucleic acids. The exonuclease may be an exonuclease cleaving nucleic acids in a 3'- to 5'-direction. The exonuclease may be Exonuclease I. Exonuclease I, as an E. coli exonuclease, cleaves a single stranded DNA in the 3'- to 5'-direction.

The term "nucleic acid polymerase" refers to an enzyme that catalyzes polymerization of nucleic acids. The first nucleic acid polymerase may be a DNA polymerase. The DNA polymerase may be T4 DNA polymerase, T7 polymerase, Klenow fragment, DNA polymerase I, Taq DNA polymerase, Bst DNA polymerase (exonuclease minus), PyroPhage 3173 DNA polymerase, Tth DNA polymerase, Pfx DNA polymerase, Tfi DNA polymerase, Tfl DNA polymerase, hot start polymerase, BcaBEST DNA polymerase, or any combination thereof.

The blunt end refers to an end of two single stranded polynucleotide chains terminating in a base pair, so that no single stranded nucleic acid is left. The telomere fragment-adaptor nucleic acid ligated product with the blunt end may be prepared using an exonuclease, a nucleic acid polymerase, or any combination thereof. For example, the exonuclease may cleave a single stranded portion of the telomere fragment-adaptor nucleic acid ligated product (e.g., region of the telomere not hybridized to the adaptor) in the 3'- to 5'-direction to prepare a telomere fragment-adaptor nucleic acid ligated product with a 5' overhang of the adaptor nucleic acid (FIG. 1B). The nucleic acid polymerase may polymerize a nucleic acid by using a 5'- or 3'-overhang of the telomere fragment-adaptor nucleic acid ligated product (e.g., the 5' overhang of the adaptor nucleic acid) as a template to prepare a telomere fragment-adaptor nucleic acid ligated product with a 5' blunt end, a 3' blunt end, or both (FIG. 1B). A process of forming a nucleic acid with a blunt end by polymerizing the nucleic acid by using an overhang as a template is referred to as a fill-in process.

The method may further include phosphorylating a 5'-end of the telomere fragment-adaptor nucleic acid ligated product with the blunt end by using a polynucleotide kinase (PNK) after preparing the telomere fragment-adaptor nucleic acid ligated product with the blunt end. An enzyme phosphorylating the 5'-end may be an enzyme well known in the art. For example, the enzyme phosphorylating the 5'-end may be a T4 polynucleotide kinase (T4 PNK) or variants thereof. Phosphorylation conditions may be selected in accordance with a selected enzyme by those of ordinary skill in the art. The phosphorylation may be performed under conditions suitable for phosphorylation of the 5'-end.

The method includes preparing a circular telomere fragment-adaptor nucleic acid ligated product by incubating the telomere fragment-adaptor nucleic acid ligated product with the blunt end in the presence of a ligase.

The ligase and the incubating are as described above.

The circular telomere fragment-adaptor nucleic acid ligated product may be formed by self-ligation by which both ends of a single strand are ligated.

The method includes amplifying the telomere fragment by incubating the circular telomere fragment-adaptor nucleic acid ligated product in the presence of a primer and a second nucleic acid polymerase.

The term "primer" refers to a short nucleic acid strand that serves as a starting point of replication of template-dependent nucleic acid synthesis. The primer may be a forward primer including a nucleic acid sequence identical to at least two continuous polynucleotides located at 5' of the first region of the single stranded adaptor, a reverse primer including a nucleic acid sequence complementary to the at least two continuous polynucleotides located at 5' of the first region of the single stranded adaptor, or a combination thereof. For example, the primer may be a pair of a forward primer including a nucleic acid sequence identical to at least two continuous polynucleotides located at 5' of the first region of the single stranded adaptor and a reverse primer including a nucleic acid sequence complementary to at least two continuous polynucleotides of the telomere. For example, the primer may be a pair of a forward primer including a nucleic acid sequence identical to at least two continuous polynucleotides of the telomere and a reverse primer including a nucleic acid sequence complementary to at least two continuous polynucleotides located at 5' of the first region of the single stranded adaptor.

The primer may have a length of about 5 nt to about 30 nt, about 7 nt to about 30 nt, about 9 nt to about 30 nt, about 12 nt to about 30 nt, about 15 nt to about 30 nt, about 17 nt to about 27 nt, or about 20 nt to about 27 nt.

The second nucleic acid polymerase may be a DNA polymerase. The DNA polymerase may be T4 DNA polymerase, T7 polymerase, Klenow fragment, DNA polymerase I, Taq DNA polymerase, Bst DNA polymerase (exonuclease minus), PyroPhage 3173 DNA polymerase, Tth DNA polymerase, Pfx DNA polymerase, Tfi DNA polymerase, Tfl DNA polymerase, hot start polymerase, BcaBEST DNA polymerase, or any combination thereof.

The term "amplification" refers to a process of increasing the number of copies of a nucleic acid and includes amplification of DNA from DNA and amplification of DNA from RNA. The amplifying of the telomere fragment may be performed using a method well known in the art. The amplifying of the telomere fragment may be performed by thermal cycling amplification, isothermal amplification, or any combination thereof. The amplifying of the telomere fragment may be performed by polymerase chain reaction (PCR), multiple displacement amplification (MDA), nucleic acid sequence based amplification (NASBA), ligase chain reaction (LCR), strand displacement amplification (SDA), rolling circle amplification (RCA), or any combination thereof. The "PCR" is a method of amplifying a target nucleic acid from a primer pair specifically binding to the target nucleic acid by using a polymerase. For example, amplification of a nucleic acid is performed by repeating a process including denaturation, annealing, and elongation. The term "annealing" and the term "hybridization" may be used interchangeably. For example, the amplifying of the telomere fragment may be performed by quantitative PCR (q-PCR). The q-PCR is a method of observing an increase in a PCR product at each cycle in real time and is used to analyze a sample by detecting and quantizing a fluorescent material that reacts to the PCR product.

The method may further include calculating a length of the telomere of the genomic DNA by measuring a length of the amplified telomere fragment. The length of the amplified telomere fragment may be measured by a method well known in the art, for example, q-PCR and electrophoresis.

A method of amplifying a telomere of genomic DNA according to another exemplary embodiment includes:

preparing a genomic DNA-adaptor nucleic acid ligated product by incubating a sample including genomic DNA including a telomere in the presence of a single stranded adaptor nucleic acid and a ligase. Here, the single stranded adaptor nucleic acid includes a first region complementary to a nucleic acid sequence of the telomere or a fragment thereof;

preparing a telomere fragment-adaptor nucleic acid ligated product by incubating the genomic DNA-adaptor nucleic acid ligated product in the presence of at least one nuclease;

preparing a telomere fragment-adaptor nucleic acid ligated product with a blunt end by incubating the telomere fragment-adaptor nucleic acid ligated product in the presence of an exonuclease, a first nucleic acid polymerase, or a combination thereof;

preparing a circular telomere fragment-adaptor nucleic acid ligated product by incubating the telomere fragment-adaptor nucleic acid ligated product with the blunt end in the presence of a ligase;

amplifying the telomere fragment by incubating the circular telomere fragment-adaptor nucleic acid ligated product in the presence of a primer and a second nucleic acid polymerase.

The primer can be a forward primer including a nucleic acid sequence identical to at least two contiguous nucleotides located 5' of the first region of the single stranded adaptor, a reverse primer including a nucleic acid sequence complementary to the at least two contiguous nucleotides located 5' of the first region of the single stranded adaptor, or a combination thereof.

The method includes preparing a genomic DNA-adaptor nucleic acid ligated product by incubating a sample containing genomic DNA including a telomere in the presence of a single stranded adaptor nucleic acid and a ligase. The telomere, the genome, the genomic DNA, the sample, the single stranded adaptor, the ligase, and the incubating are as described above.

The genomic DNA-adaptor nucleic acid ligated product is a ligated product in which the telomere of the genomic DNA is ligated to the adaptor nucleic acid. The method includes preparing a telomere fragment-adaptor nucleic acid ligated product by incubating the genomic DNA-adaptor nucleic acid ligated product in the presence of at least one nuclease. In some aspects, only one adaptor is ligated to one end of the genomic DNA fragment, such that the genomic DNA fragment-adaptor nucleic acid ligated product comprises only one adaptor sequence ligated to one end of the genomic DNA.

The nuclease, the incubating, and the telomere fragment-adaptor nucleic acid ligated product are as described above.

The method includes preparing a telomere fragment-adaptor nucleic acid ligated product with a blunt end by incubating the telomere fragment-adaptor nucleic acid ligated product in the presence of an exonuclease, a first nucleic acid polymerase, or a combination thereof. The exonuclease, the first nucleic acid polymerase, the incubating, the blunt end, and the telomere fragment-adaptor nucleic acid ligated product with a blunt end are as described above.

The method includes preparing a circular telomere fragment-adaptor nucleic acid ligated product by incubating the telomere fragment-adaptor nucleic acid ligated product with the blunt end in the presence of a ligase. The ligase, the incubating, and the circular telomere fragment-adaptor nucleic acid ligated product are as described above.

The method includes amplifying the telomere fragment by incubating the circular telomere fragment-adaptor nucleic acid ligated product in the presence of a primer and a second nucleic acid polymerase. The primer, the second nucleic acid polymerase, the incubating, and the amplifying are as described above.

The method may further include calculating a length of the telomere of the genomic DNA by measuring a length of the amplified telomere fragment. Such a method is as previously described herein.

A composition for amplifying a telomere of genomic DNA according to another exemplary embodiment includes a single stranded adaptor nucleic acid including a first region complementary to a nucleic acid sequence of the telomere or a fragment thereof. The telomere nucleic acid sequence, the first region, the single stranded adaptor nucleic acid, the genome, the genomic DNA, the telomere, and the amplifying are as described above.

The composition may include an adaptor nucleic acid including a first region with a nucleic acid sequence of SEQ ID NO: 2, an adaptor nucleic acid including a first region with a nucleic acid sequence of SEQ ID NO: 3, an adaptor nucleic acid including a first region with a nucleic acid sequence of SEQ ID NO: 4, an adaptor nucleic acid including a first region with a nucleic acid sequence of SEQ ID NO: 5, an adaptor nucleic acid including a first region with a nucleic acid sequence of SEQ ID NO: 6, an adaptor nucleic acid including a first region with a nucleic acid sequence of SEQ ID NO: 7, or any combination thereof.

A kit for amplifying a telomere of genomic DNA according to another exemplary embodiment includes a single stranded adaptor nucleic acid including a first region complementary to a nucleic acid sequence of the telomere or a fragment thereof, and a primer. The primer is a forward primer including a nucleic acid sequence identical to at least two continuous polynucleotides located at 5' of the first region of the single stranded adaptor, a reverse primer including a nucleic acid sequence complementary to the at least two continuous polynucleotides located at 5' of the first region of the single stranded adaptor, or a combination thereof.

The telomere nucleic acid sequence, the first region, the single stranded adaptor nucleic acid, the primer, the genome, the genomic DNA, the telomere, and the amplifying are as described above.

The kit may further include a ligase, a nucleic acid polymerase, an exonuclease, and a combination thereof. The ligase, the nucleic acid polymerase, and the exonuclease are as described above.

According to the method of amplifying a telomere of genomic DNA and a composition and a kit for amplifying the telomere of the genomic DNA used therefor according to an exemplary embodiment, reaction efficiency may be improved by using one adaptor, amplification efficiency of the telomere region may be improved by reducing amplification of the other region of the genomic DNA except for the telomere, the amplified telomere fragment may simply be detected with high sensitivity without performing an additional process such as Southern blotting, and a length of a single telomere may be measured by amplifying a single chromosomal telomere.

Figure 1A:
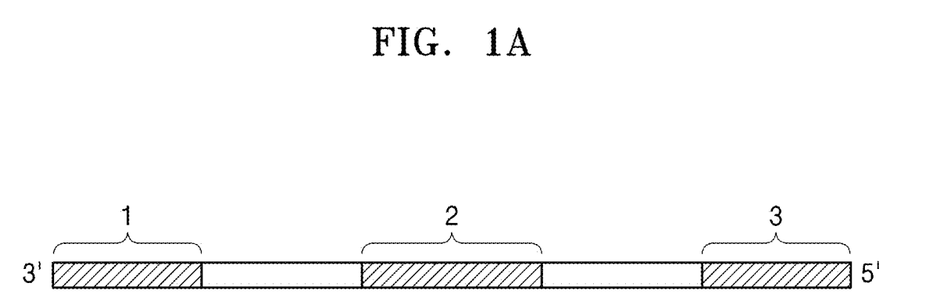
FIG. 1A is a schematic diagram of an adaptor polynucleotide (1: annealing region (first region), 2: forward primer region (second region), 3: reverse primer binding region (third region)
Figure 1B:
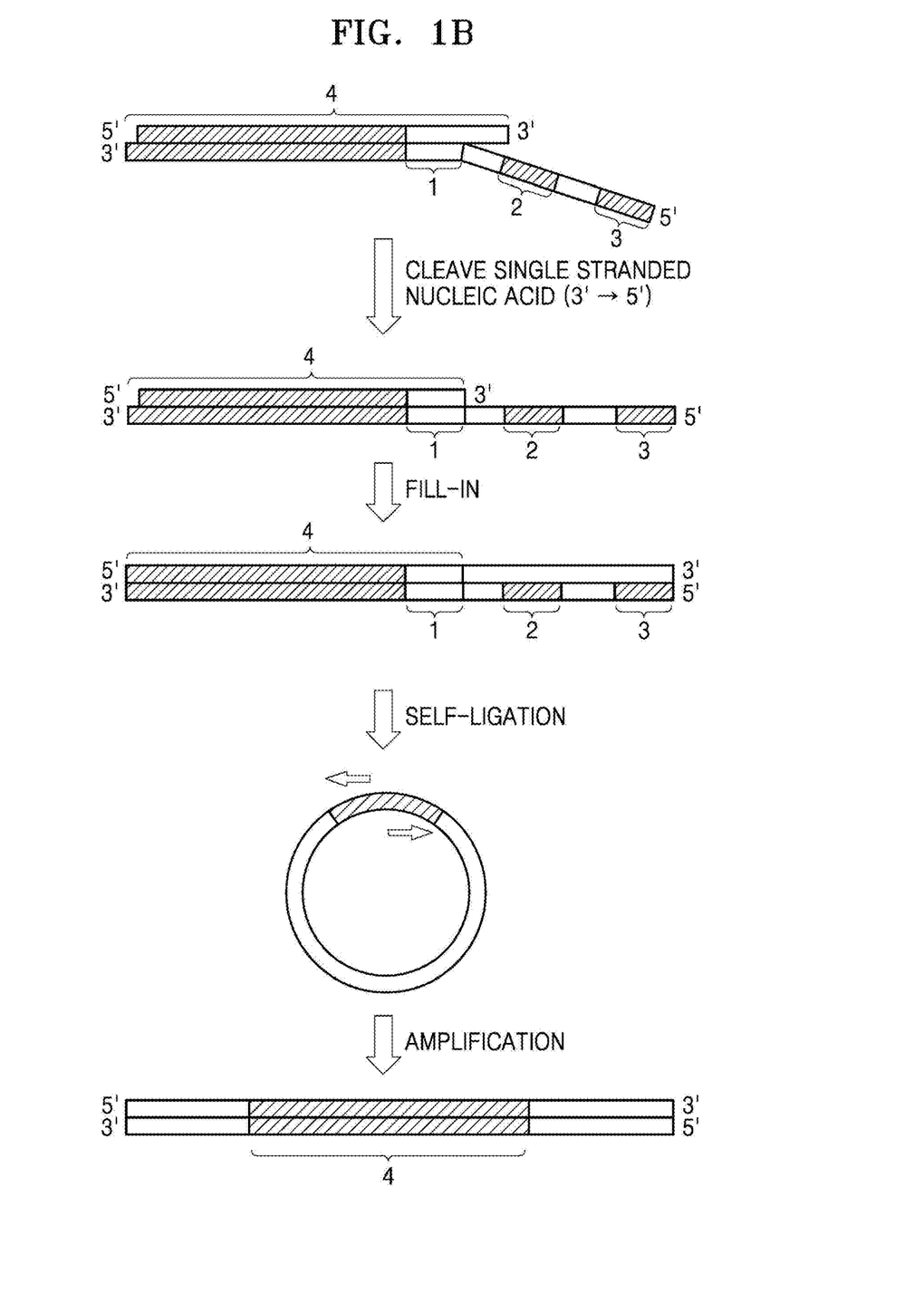
FIG. 1B is a schematic diagram of a method of amplifying a telomere according to an exemplary embodiment (1: annealing region (first region), 2: forward primer region (second region), 3: reverse primer binding region (third region), and 4: telomere region))

Exemplary polynucleotides for use in the methods, compositions, and kits described herein may comprise, but are not limited to the polynucleotides illustrated in FIGS. 1A and 1B, wherein: 1 is a annealing region (first region) of a single-stranded adaptor nucleic acid; 2 is a forward primer region (second region) of the single-stranded adaptor nucleic acid; 3 is a reverse primer binding region (third region) of the single-stranded adaptor nucleic acid; and 4 is a telomere region of the single-stranded adaptor nucleic acid (unshaded: terminal 3' single-stranded overhang of telomere, shaded: double stranded tandem repeats of telomere).

Hereinafter, one or more embodiments of the present inventive concept will be described in detail with reference to the following examples. These examples are not intended to limit the purpose and scope of the one or more embodiments of the present inventive concept.

Example 1: Amplification of Telomere and Measurement of Length Thereof 1-1: Preparation of Adaptor Polynucleotide and Primer Pair Adaptor polynucleotides each including an annealing region binding to a telomere region, a forward primer region including the same sequence as a forward primer sequence, and a reverse primer-binding region including a nucleic acid sequence complementary to a reverse primer sequence were prepared.

Nucleic acid sequences of the adaptor polynucleotides and the primer pair are shown in Table 1 below.

TABLE 1

| Name | Nucleic acid sequence |
|---|---|
| Telo-adaptor 1 | 5'-AGATCGGAAGAGCTCGTATGCTGCTCCGTGCATCTGG CATCCCCTAAC-3' (SEQ ID NO: 8) |
| Telo-adaptor 2 | 5'-AGATCGGAAGAGCTCGTATGCTGCTCCGTGCATCTGG CATCTAACCCT-3' (SEQ ID NO: 9) |
| Telo-adaptor 3 | 5'-AGATCGGAAGAGCTCGTATGCTGCTCCGTGCATCTGG CATCTCTAACC-3' (SEQ ID NO: 10) |
| Telo-adaptor 4 | 5'-AGATCGGAAGAGCTCGTATGCTGCTCCGTGCATCTGG CATCTTAACCC-3' (SEQ ID NO: 11) |
| Telo-adaptor 5 | 5'-AGATCGGAAGAGCTCGTATGCTGCTCCGTGCATCTGG CATCTACCCTA-3' (SEQ ID NO: 12) |
| Telo-adaptor 6 | 5'-AGATCGGAAGAGCTCGTATGCTGCTCCGTGCATCTGG CATCTCCCTAA-3' (SEQ ID NO: 13) |
| Forward primer | 5'-TGCTCCGTGCATCTGGCATCT-3' (SEQ ID NO: 14) |
| Reverse primer | 5'-GCATACGAGCTCTTCCGATCT-3' (SEQ ID NO: 15) |

1-2: Cleavage of Genomic DNA

Genomic DNA was cleaved using a restriction enzyme to obtain a telomere region.

Particularly, 1 µg of genomic DNA (Promega, G1471), 20 units of MseI (NEB, R0525L), 20 units of NdeI (NEB, R0111L), 1×NEB buffer 2 (NEB), and water were mixed to prepare 100 µl of a reaction mixture. The prepared reaction mixture was incubated at 37° C. for 3 hours to cleave the genomic DNA.

1-3: Ligation of Adaptor Polynucleotide

An adaptor polynucleotide was ligated to the genomic DNA cleaved by the restriction enzyme.

Particularly, 100 ng of the genomic DNA cleaved by the restriction enzyme prepared according to Example 1-2, 100 pmol of each of Telo-adaptors 1 to 6 listed in Table 1, 2000 units of a T4 DNA ligase (NEB, MO202M), 1× reaction buffer solution (NEB), 1 mM of ATP (NEB, #9804), and water were mixed to prepared 100 µl of a reaction mixture. The prepared reaction mixture was incubated at 16° C. for 12 hours to ligate the adaptor polynucleotide to the genomic DNA.

1-4. Cleavage of Single Stranded Nucleic Acid and Fill-in

The single stranded nucleic acid was cleaved in the 3'- to 5'-direction from a telomere-adaptor polynucleotide ligated product, and a fill-in process was performed to prepare a polynucleotide with a blunt end.

Particularly, 100 ng of the genomic DNA to which the adaptor polynucleotide prepared according to Example 1-3 is ligated, 20 units of Exonuclease I (*E. coli*)(NEB, MO293L), 50 units of a Klenow fragment (NEB, MO210L), 1× NEBuffer2 (NEB), 33 µM of dNTP (NEB, N04475), and water were mixed to prepare 100 µl of a reaction mixture. The prepared reaction mixture was incubated at 25° C. for 1 hour to prepare adaptor polynucleotide-ligated genomic DNA with a blunt end. Since the 3'-end of the telomere has a long single stranded region, it is difficult to form a blunt end. Thus, the fill-in process by the Klenow fragment was facilitated using a single strand-specific 3'->5' exonuclease. A linear exonuclease adaptor polynucleotide-genomic DNA ligated product may be obtained by cleavage of the single stranded nucleic acid and the fill-in process.

1-5. Self-Ligation

A circular adaptor polynucleotide-genomic DNA was prepared by self-ligating the adaptor polynucleotide-ligated genomic DNA with the blunt end.

Particularly, 100 ng of the adaptor polynucleotide-ligated genomic DNA prepared according to Example 1-4, 20 units of a T4 polynucleotide kinase (PNK) (NEB, MO201 L), 1× reaction buffer (70 mM Tris-HCl, 10 mM MgCl$_2$, 5 mM DTT) (NEB), 1 mM of ATP (NEB, #9804), and water were mixed to prepare 100 µl of a reaction mixture. The prepared reaction mixture was incubated at 37° C. for 1 hour, and then incubated at 65° C. for 20 minutes.

Then, 1 µl (2000 units) of a T4 DNA ligase was added to the reaction mixture.

The reaction mixture was incubated at 25° C. for 1 hours to perform self-ligation of the adaptor polynucleotide-ligated genomic DNA. Via self-ligation, a circular adaptor polynucleotide-genomic DNA ligated product may be prepared.

1-6. Amplification of Telomere

The telomere of the genomic DNA was amplified by amplifying the circular adaptor polynucleotide-genomic DNA prepared by self-ligation using a primer pair amplifying outward from the adaptor polynucleotide.

Particularly, 1 ng of the circular adaptor polynucleotide-genomic DNA ligated product prepared according to Example 1-5 or the linear adaptor polynucleotide-genomic DNA ligated product prepared according to Example 1-4, 10 µM of a forward primer (SEQ ID NO: 14), 10 µM a reverse primer (SEQ ID NO: 15), 10 µl of LightCycler 480 SYBR Green 1 master (ROCHE, 04-887-352-001), and water were mixed to prepare 20 µl of a reaction mixture. The prepared reaction mixture was subjected to PCR in a Lightcycler 480 (Roche). The PCR was performed by repeating 50 cycles, each cycle including incubation at 95° C. for 10 seconds, 55° C. for 10 seconds, and at 72° C. for 1.5 minutes. Amplification of the telomere region in comparison with amplification of genomic DNA was confirmed using the following primer pair amplifying of C-gene (control gene) of genomic DNA as a control group.

```
Forward primer:
                                     (SEQ ID NO: 16)
5'-CAGCAAGTGGGAAGGTGTAATCC-3'

Reverse primer:
                                     (SEQ ID NO: 17)
5'-CCCATTCTATCATCAACGGGTACAA-3'
```

Figure 2A:
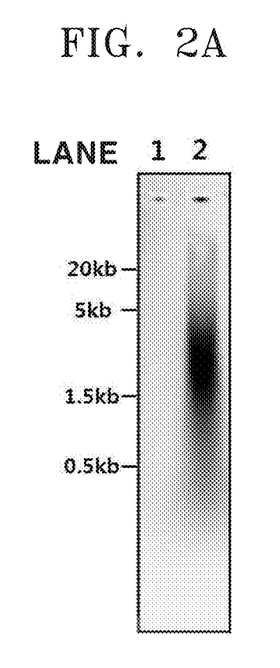
FIG. 2A is an electrophoresis image of products of quantitative PCR (Lane 1: amplification of nucleic acid before self-ligation and Lane 2: amplification of nucleic acid after self-ligation)
Figure 2B:
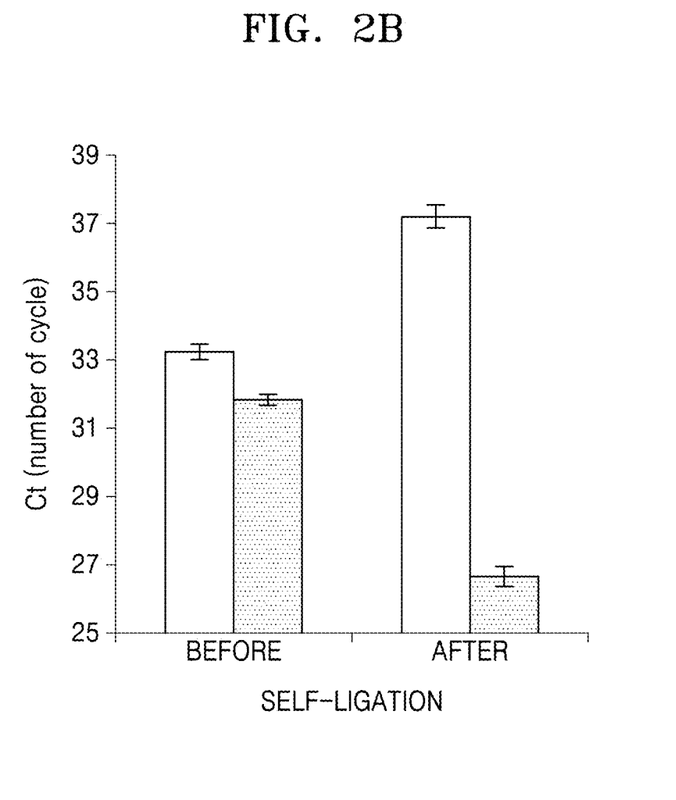
FIGS. 2B and 2C are graphs of cycle threshold (Ct) and amplification fold by quantitative PCR (White bar: C-gene and Dotted bar: telomere).
Figure 2C:
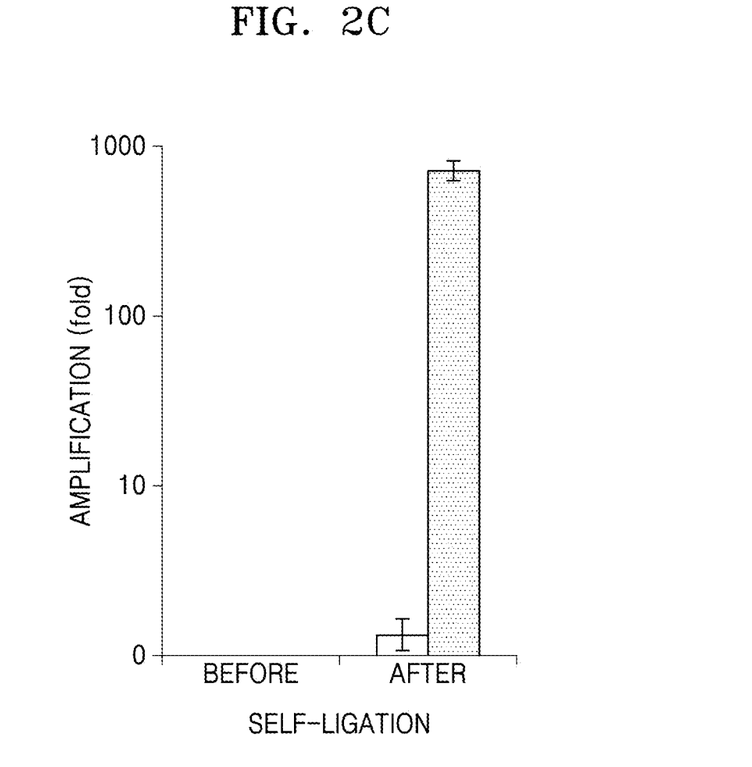

Reaction products of q-PCR were subjected to electrophoresis to identify whether the telomere region is amplified. FIG. 2A illustrates the results of electrophoresis of the reaction products of q-PCR (Lane 1: amplification of nucleic acid before self-ligation and Lane 2: amplification of nucleic acid after self-ligation). FIGS. 2B and 2C illustrate graphs of cycle threshold (Ct)(number of cycle) and amplification fold by q-PCR (White bar: C-gene and Dotted bar: telomere)

As illustrated in FIG. 2A, it was confirmed that the telomere region was amplified as a result of amplifying the nucleic acid after self-ligation. In addition, as illustrated in FIGS. 2B and 2C, the telomere region was amplified in comparison with the genomic DNA.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of amplifying a telomere of genomic deoxyribonucleic acid (DNA), the method comprising:
preparing a telomere fragment by incubating a sample comprising genomic DNA including a telomere with at least one nuclease, wherein the nuclease is a restriction enzyme and cleaves the genomic DNA to produce a telomere fragment having 3'-overhang;
preparing a ligated telomere fragment by incubating the telomere fragment with at least one single-stranded adaptor nucleic acid and a ligase, wherein the at least one single-stranded adaptor nucleic acid comprises a first region located at the 3' end of the single stranded adaptor nucleic acid that is complementary to a nucleic acid sequence on the 3' overhang of the telomere fragment, thereby forming an annealed product between the telomere fragment and the single-stranded adaptor nucleic acid, and ligating the telomere fragment to the single-stranded adaptor nucleic acid in the annealed product to form the ligated telomere;
preparing a blunt-end ligated telomere fragment by incubating the ligated telomere fragment with a single-strand specific exonuclease that cleaves in the 3' to 5' direction, a first nucleic acid polymerase, or a combination thereof;
preparing a circular telomere fragment by incubating the blunt-end ligated telomere fragment with a ligase, thereby ligating the 5' end of the one strand with the 3' end of the same strand and the 3' end of the other strand with the 5' end of the same strand; and
amplifying the telomere fragment by incubating the circular telomere fragment with a forward primer, a reverse primer, or a combination thereof, and a second nucleic acid polymerase,
wherein the forward primer comprises a nucleic acid sequence identical to at least two contiguous nucleotides located 5' of the first region of the single-stranded adaptor nucleic acid and the reverse primer comprises a nucleic acid sequence complementary to the at least two contiguous nucleotides located 5' of the first region of the single-stranded adaptor nucleic acid.

2. The method of claim 1, wherein the sample is a biological sample.

3. The method of claim 1, wherein the single-stranded adaptor nucleic acid further comprises a second region comprising a nucleic acid sequence identical to the nucleic acid sequence of the forward primer, and a third region comprising a nucleic acid sequence complementary to the reverse primer, from a 3'-end of the adaptor nucleic acid.

4. The method of claim 1, wherein the first region comprises a nucleic acid sequence selected from the group consisting of SEQ ID NOS: 2 to 7.

5. The method of claim 1, wherein the exonuclease is Exonuclease I.

6. The method of claim 1, wherein the first nucleic acid polymerase and/or the second nucleic acid polymerase is a DNA polymerase.

7. The method of claim 1, further comprising phosphorylating a 5'-end of the ligated telomere fragment comprising a blunt end by incubating said ligated telomere fragment comprising a blunt end with a polynucleotide kinase (PNK).

8. The method of claim 1, wherein amplifying the telomere fragment is performed by a thermal cycling amplification method or an isothermal amplification method.

9. The method of claim 1, wherein the amplifying of the telomere fragment is performed by a polymerase chain reaction (PCR), multiple displacement amplification (MDA), nucleic acid sequence based amplification (NASBA), ligase chain reaction (LCR), strand displacement amplification (SDA), rolling circle amplification (RCA), or a combination thereof.

* * * * *